United States Patent [19]

Lesley

[11] Patent Number: 5,780,270
[45] Date of Patent: Jul. 14, 1998

[54] SITE-SPECIFIC MUTAGENESIS AND MUTANT SELECTION UTILIZING ANTIBIOTIC-RESISTANT MARKERS ENCODING GENE PRODUCTS HAVING ALTERED SUBSTRATE SPECIFICITY

[75] Inventor: Scott A. Lesley, Oregon, Wis.

[73] Assignee: Promega Corporation, Madison, Wis.

[21] Appl. No.: 682,073

[22] Filed: Jul. 17, 1996

[51] Int. Cl.$^6$ .......................... C12P 19/34; C07H 21/04; C12Q 1/68; C12N 15/09
[52] U.S. Cl. .......................... 435/91.1; 435/6; 435/320.1; 435/810; 536/22.1; 536/23.7
[58] Field of Search .......................... 435/6, 810, 91.2, 435/91.1, 320.1; 536/23.1, 22.1

[56] References Cited

U.S. PATENT DOCUMENTS

| | | | |
|---|---|---|---|
| 4,521,509 | 6/1985 | Benkovic et al. | 435/6 |
| 4,873,192 | 10/1989 | Kunkel | 435/172.3 |
| 5,071,743 | 12/1991 | Slilaty | 435/172.3 |

FOREIGN PATENT DOCUMENTS

| | | | |
|---|---|---|---|
| 0 397 463 A3 | 11/1990 | European Pat. Off. | C12N 15/10 |
| 4024187 | 7/1993 | Germany . | |
| WO 93/13216 | 7/1993 | WIPO . | |

OTHER PUBLICATIONS

Venkatachalam et al., Characterization of TEM-1 bata-lactamase mutants from positions 238-241 with increased catalytic efficiency for ceftazidime, J. Biol. Chemistry, vol. 269(38), pp. 23444-23450, 1994.

Bohnsack (1996), Methods in Molecular Biology: In vitro Mutagenesis Protocols: vol. 57, M.K. Thrower, Ed, Humana Press Inc., Totowa, New Jersey.

Current Protocols in Molecular Biology (1994), vol. 1, Chapter 1.8, John Wiley and Sons, New York, New York.

Delaire, M., Labia, R., Samama, J.P., and Masson, J.M. (1992), The Journal of Biological Chemistry 267(29): 20600–20606.

Hanahan, D. (1985), In: DNA Cloning, vol. 1, Glover, ed., IRL Press Ltd., London, 109.

Imtiaz et al. (1994), Antimicrobial Agents and Chemotherapy, (38)5: 1134–1139.

Lenfant et al. (1991), The Journal of Biological Chemistry, 266(26):17187–17194.

Palzkill and Botstein (1992a), Proteins: Structure, Function, and Genetics, 14:29–44.

Palzkill and Botstein (1992b), Journal of Bacteriology, 17:5237–5243.

Vandeyar et al. (1988), Gene, 65:129–133.

Venkatachalam et al. (1994), Characterization of TEM-1 β-lactamase Mutants From Positions 238 to 241 With Increased Catalytic Efficiency For Ceftazidime, The Journal of Biological Chemistry, 269(38): 23444–23450.

Primary Examiner—Kenneth R. Horlick
Assistant Examiner—Joyce Tung
Attorney, Agent, or Firm—DeWitt Ross & Stevens SC

[57] ABSTRACT

Methods, kits, and reagents for conducting site-specific mutagenesis of single or double-stranded nucleic acids which utilizes novel antibiotic resistance conferred by a mutated antibiotic resistance gene for efficient mutant selection are described.

14 Claims, 2 Drawing Sheets ns cell line.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCGCGAGACC CACCCTTGGA GGCTCCAGAT TTATC         3 5

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATAAATCTG GAGCCTCCAA GGGTGGGTCT CGCGG         3 5

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGCCAGGGTT CCCAGTCACG ACG 23

( 2 ) INFORMATION FOR SEQ ID NO:4:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:4:

CGTCGTGACT GGGAACCCTG GCG 23

( 2 ) INFORMATION FOR SEQ ID NO:5:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:5:

GCCGGGCCTC TTGCGGGCGT CCATTCC 27

SITE-SPECIFIC MUTAGENESIS AND MUTANT SELECTION UTILIZING ANTIBIOTIC-RESISTANT MARKERS ENCODING GENE PRODUCTS HAVING ALTERED SUBSTRATE SPECIFICITY

FIELD OF THE INVENTION

The present invention is drawn to a method for the efficient generation and selection of site-specific deoxyribonucleic acid (DNA) and ribonucleic acid (RNA) mutants.

BIBLIOGRAPHY

Full bibliographic citations to the references described hereinbelow can be found in the Bibliography, immediately preceding the Sequence Listing.

DESCRIPTION OF THE PRIOR ART

The scientific literature describes several methods for generating and selecting mutated nucleic acid sequences. These methods utilize different types of selection to increase the efficiency of mutagenesis. For instance, Bohnsack (1996) describes a method for site-directed mutagenesis which has been given the name Altered Sites II. The Altered Sites II mutagenesis protocol uses antibiotic resistance to select the successfully mutated transformants. In this protocol, a mutagenic oligonucleotide and an oligonucleotide that restores a frame-shift in an antibiotic resistance gene (referred to as the "repair" oligonucleotide) are simultaneously annealed to a template DNA strand which is either single-stranded DNA or alkaline-denatured double-stranded DNA. The complementary mutant strand is then synthesized using T4 DNA polymerase, and T4 DNA ligase.

The mutant plasmids are then replicated in a mismatched repair-deficient E. coli mutant strain (either ES1301 or BMH 71–18). Replicated plasmids are then segregated by transforming into a second host, such as JM109. The key to this selection method is that the antibiotic resistance gene is initially non-functional. Activation of the gene provides the means for selection. However, a second antibiotic resistance gene is also required to effect the selection. This requires that specialized plasmids be used in the Altered Sites II protocol. Another notable feature of this protocol is that a third oligonucleotide which inactivates a second antibiotic resistance trait can be incorporated into the plasmid. By alternating repair and inactivation of the antibiotic resistance genes in the vectors, multiple rounds of mutagenesis can be performed without the need for additional subcloning steps.

Vandeyar et al. (1988) describe an in vitro selection procedure for mutagenesis utilizing selective methylation of the mutant strand via incorporation of 5-methyl-dCTP. Site-directed mutagenesis is typically performed by annealing an oligonucleotide from 15–20 bases long to a single-stranded template. The oligonucleotide is then extended using DNA polymerase, and the ends of the strand are ligated. This yields a hetero-duplex molecule which contains a mismatched base pair at the mutation site.

In the Vandeyar et al. method, after annealing of the mutagenic oligonucleotide, the primer strand is extended in a polymerase cocktail containing 5-methyl-dCTP. Methylated DNA is resistant to cleavage by the restriction enzyme MspI. Because only the mutant strand contains 5-methyl-dCTP, digestion of the hetero-duplex with MspI results in selective cleavage of the template strand. After nicking the template strand by MspI digestion, treatment with exonuclease III removes the non-mutant strand. The remaining mutant strand is then used to transform competent E. coli. This method is notable in that the selection of the mutant strand is done by in vitro enzymatic digestion.

Benkovic et al., U.S. Pat. No. 4,521,509, describe a method for degrading DNA in which a mutated strand includes 2'-deoxyadenosine-5'-O-(1)-thiotriphosphate. The phosphorothioate internucleotide linkages are resistant to exonuclease III digestion. This allows the parent strand to be degraded, while the mutant strand remains intact and can be used to transform suitably competent host cells.

Another method of site-specific DNA mutagenesis and selection is described by Kunkel in U.S. Pat. No. 4,873,192. In this method, uracil-substituted template DNA strands are prepared by propagating the initial DNA plasmid template in a strain of E. coli which yields uracil-substituted DNA templates. Following annealing and extension of a mutant strand to the dUTP-containing template strand, the plasmid is transformed into an E. coli strain which produces dUTPase, whereby the template strand is digested while the mutant strain remains intact. See also, European Patent Application No. 397 463 A3 to the Eastman Kodak Company.

Slilaty, U.S. Pat. No. 5,071,743, describes a method of site-directed mutagenesis which yields a mutant formation efficiency of about 50%. This reference describes a process wherein a mutagenic oligonucleotide and a "closing" oligonucleotide are hybridized to a single-stranded linear DNA template. The "closing" oligonucleotide has a sequence which is complementary to either end of the linear DNA template and functions to circulize the DNA template. Upon circulization, the "closing" oligonucleotide forms an initiation site for polymerase-dependent complementary-strand synthesis. The complementary DNA strand, including the hybridized mutagenic and "closing" oligonucleotides is then formed using polymerase and ligase enzymes. The plasmids so formed are then transformed into a suitable host for replication. Similar to Kunkel, above, mutant selection is accomplished by propagating the initial DNA plasmid template in a strain of E. coli which yields uracil-substituted DNA templates. The semi-conservative replication of DNA then allows mutant selection based upon the decreased biological activity of uracil-substituted DNA in the ultimate transformed cell line.

Another method of increasing the efficiency of site-directed mutagenesis is described in PCT published application Serial No. WO 93/13216. Here, a target DNA containing a unique restriction site is used to generate a mismatched mutant strand which lacks the restriction site. The resultant heteroduplex is then transformed into a suitable host. After several rounds of replication, the plasmid DNA is isolated from the transformed host. The isolated DNA is then treated with an enzyme which cleaves at the unique restriction site, thereby cleaving only plasmid derived from the non-mutated parental DNA strand. Suitably competent cells are then transformed using the digested DNA. The uncleaved mutant DNA is more readily transformed into the cells than the cleaved parental DNA, thereby increasing the yield of successfully transformed mutants.

German Patent 4,024,187, describes a method for site-directed mutagenesis wherein a plasmid is cleaved at a cleavage site which is outside the region to be mutated. The cleavage site is then modified so that it can no longer be closed by a ligase. Then, with a second aliquot of the plasmid, the region to be mutated is excised from the plasmid and the residual plasmid isolated. The plasmid with the altered cleavage site and the plasmid with the mutation region excised are then mixed and rehybridized to form two partially single-stranded complementary gapped circles which contain the region to be mutated in single-stranded form. A mutagenic oligonucleotide can then be hybridized into the open gap.

β-Lactamase is a clinically important enzyme because of its degradative action on several widely used antibiotics. Consequently, its structure and function have been extensively studied. Several such studies are described below.

Palzkill and Botstein (1992a) describe a structure/function analysis of β-lactamase utilizing random mutagenesis of short stretches of the β-lactamase gene. In this study, three to six codons of a DNA sequence coding β-lactamase were randomly mutagenized. The mutant DNA's were then transformed into a suitable host and the percentage of random sequences which produce a functional protein determined.

A similar study of Palzkill and Botstein (1992b) describes amino acid substitutions in TEM-1 β-lactamase which alter the substrate specificity of the β-lactamase.

Several analogous studies are described in the scientific literature. For instance, Delaire et al. (1992) described site-directed mutagenesis at the codons coding for arginine 244 and methionine 69 of β-lactamase. Venkatachalam et al. (1994) describe several broad spectrum β-lactamase mutant enzymes which display increased catalytic action against both penicillins and cephalosporins. The mutants were constructed via cassette mutagenesis and identified by substitutions in the active site which altered substrate specificity. Imtiaz et al. (1994) describe the interaction of two specific point mutations in TM-1 β-lactamase. In this study, arginine-244 was mutated to serine, along with an identical mutation at residue 164. A similar study analyzing the replacement of lysine-234 with arginine is described by Lenfant et al. (1991).

SUMMARY OF THE INVENTION

One aspect of the present invention is drawn to a method for conducting site-specific mutagenesis of single or double-stranded nucleic acids. The method includes the steps of hybridizing a first mismatched oligonucleotide which encodes a mutation in an antibiotic resistance gene to a target nucleic acid strand. Additionally, at least one other mismatched oligonucleotide encoding a desired mutation is hybridized to the target nucleic acid strand. The two hybridizations are preferably performed simultaneously. Then the hybridized mismatched oligonucleotides are extended. The resultant nucleic acid molecule is then incorporated into a host cell line to yield transformed cells. The transformed cells are then separated from non-transformed parent-type cells via a differential antibiotic resistance which is conferred to the transformed cells by the mutation encoded by the first mismatched oligonucleotide.

Another aspect of the invention is directed to a deoxyribonucleic acid comprising a nucleotide base sequence as shown in SEQ. ID. NO: 1.

A still further aspect of the present invention is a mutant gene encoding a mutation in a β-lactamase gene product which confers increased β-lactam antibiotic resistance to hosts transformed therewith comprising a nucleotide base sequence as shown in SEQ. ID. NO: 1.

Additionally, the present invention is drawn to a kit for conducting site-specific mutagenesis of single or double-stranded nucleic acids by the above-described method. The kit includes a first receptacle containing a DNA molecule selected from the group consisting of SEQ. ID NO: 1 and SEQ. ID. NO: 2, and instructions for use of the kit. The instructions are a step-by-step guide to the site-directed mutagenesis protocol described herein.

A distinct advantage of the present invention is that selection based upon the novel antibiotic resistance conferred by the first oligonucleotide dramatically increases the mutagenesis efficiency for the other mutated oligonucleotides which are incorporated into the synthesized strand. Desired mutants can be generated efficiently and quickly, in yields well in excess of 50%.

Further aims, objects, and advantages of the mutagenesis protocol described and claimed herein will become apparent upon a complete examination of the Detailed Description, attached claims, and accompanying drawing figures.

DETAILED DESCRIPTION OF THE INVENTION

Figure 1:
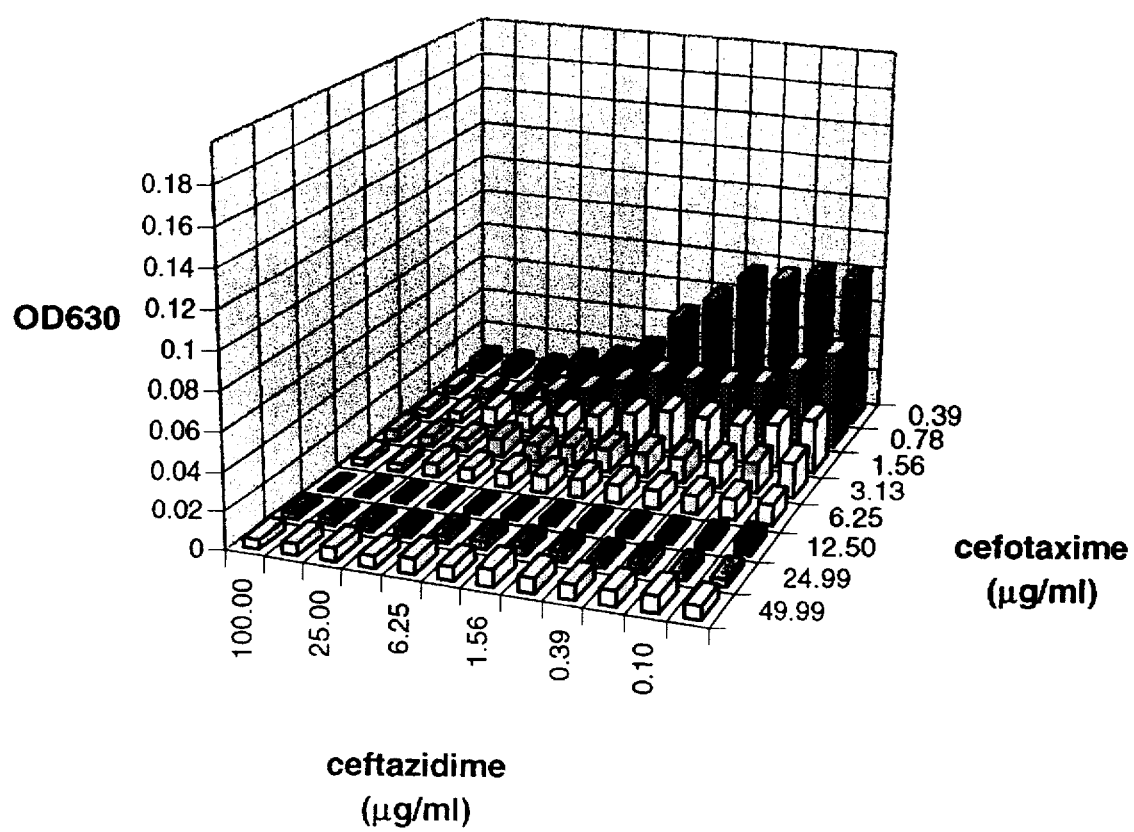
FIG. 1 is an antibiotic matrix depicting the effect of various concentrations of ceftazidime and cefotaxime on the growth of E. coli transformed with a plasmid containing the wild-type β-lactamase gene.

The first step of the method of the present invention is to hybridize a first mismatched oligonucleotide which encodes a mutation in an antibiotic resistance gene to a target nucleic acid strand. It is this first mismatched oligonucleotide which acts as a selection tool for efficiently separating successfully transformed and mutated progeny from parent-type progeny.

The mutation in the antibiotic resistance gene encoded by the first mismatched oligonucleotide confers a novel increased antibiotic resistance to hosts transformed with the gene. The increased antibiotic resistance conferred by the first oligonucleotide is not displayed in the wild-type of the organism transformed using the oligonucleotide. The preferred first mismatched oligonucleotide encodes a mutation in the enzyme gene product β-lactamase. This mutant gene product confers increased resistance to β-lactam antibiotics as compared to wild-type β-lactamase genes. Preferably, the mutation encoded by the first oligonucleotide yields a gene product which confers increased resistance to cefotaxime, ceftazidime, or both.

Additionally, at least one other mismatched oligonucleotide encoding a desired mutation is hybridized to the target nucleic acid strand. It is critical for optimum performance of the method that the desired mutation encoded by the at least one other oligonucleotide hybridizes to the same target nucleic acid strand as the first mismatched oligonucleotide. Also, the desired mutation encoded by the at least one other oligonucleotide should not interfere with the functionality of the first hybridized oligonucleotide. Therefore, it is preferred that the at least one other oligonucleotide hybridizes to a different physical location on the target nucleic acid strand than the first oligonucleotide.

The desired mutation encoded by the at least one other oligonucleotide can be any mutation of interest to the user of the invention. So long as the mutation encoded by the at least one other oligonucleotide does not interfere with the functionality of the first oligonucleotide and can be hybridized to the same nucleotide strand as the first oligonucleotide, any mutation, without limitation, can be studied using the subject invention.

The two hybridizations are preferably performed simultaneously, although they may be performed in separate steps, in any order. Hybridization can be accomplished by any of several methods well known to those having skill in the art. (Reference is made to the Examples, below, for an illustrative method.)

Once the mismatched oligonucleotides have been hybridized to the same target nucleic acid strand, the oligonucleotides are extended. The extension is preferably performed using a polymerase enzyme, such as T4 DNA polymerase, and a ligase enzyme, such as T4 DNA ligase, in a suitable reaction solution including dNTPs, to yield a nucleic acid molecule which includes the two mismatched oligonucleotides within the same strand of the molecule. Such extension reactions are well known in the art. (See the Examples, below, for a preferred method of extending the hybridized oligonucleotides.)

After extension, the nucleic acids are incorporated into a suitable host. Preferably, the host is an *E. coli.* cell line. The *E. coli* cell line is preferably mismatch repair-deficient (for efficiency), although this is not required. The nucleic acid is more preferably transformed into *E. coli.* cell line ES1301. This cell line contains a mutation in the mutS gene which reduces mismatch repair in the cell, which results in a higher percentage of the desired mutation being formed.

Incorporation into a host cell line to yield transformed cells can be accomplished by any of several well known methods, including transformation using calcium chloride, electroporation, and the like. For an exhaustive description of methods for cell transformation, see *Current Protocols in Molecular Biology*, Vol 1, Chapter 1.8, incorporated herein by reference for its teaching of cellular transformation.

Successfully transformed cells will include both the mutated antibiotic resistance conferred by the first mismatched oligonucleotide, as well as the desired mutation encoded by the at least one other mismatched oligonucleotide. As a result, the successfully transformed cells can be easily separated from non-transformed parent-type cells, as well as cells which do not contain the mutation encoded by the first oligonucleotide, by the differential antibiotic resistance conferred to the transformed cells by the first mismatched oligonucleotide. This outcome greatly simplifies generating and selecting site-specific mutations.

A preferred first oligonucleotide, SEQ. ID. NO: 1, and its reverse complement, SEQ. ID. NO: 2, are depicted in Table 1, below. These two oligonucleotides confer increased β-lactam antibiotic resistance to *E. coli.* As genes incorporated into competent *E. coli,* genes having the base sequences shown in SEQ. ID. NOS. 1 and 2 provide highly useful selection markers for use in site-directed mutagenesis and mutant selection.

The present invention also includes a kit for easily carrying out the above-described protocol. The kit includes at least one receptacle which contains a nucleic acid having a base sequence as shown in SEQ. ID. NO. 1 or SEQ. ID. NO. 2. The kit also includes instructions on how to properly practice the method of the present invention.

EXAMPLES

The following Examples are included herein solely to provide a more clear and complete understanding of the invention described and claimed herein. The Examples do not limit the scope of the claimed invention in any manner whatsoever.

Example 1

The procedure described hereinabove was used to generate a mutation in the plasmid pBR322. The pBR322 plasmid contains the gene for β-lactamase and also a resistance gene for tetracycline. The subject procedure was used to alter the substrate specificity of the β-lactamase to confer resistance to ceftazidime and cefotaxime. A second mutation was introduced in the pBR322 plasmid to produce a frame-shift in the tetracycline resistance gene which inactivates the gene product. Cells containing the plasmid with the frame-shift in the tetracycline resistance gene do not grow in the presence of tetracycline. The percentage of plasmids containing this second mutation can easily be determined by evaluating the number of plasmid-containing colonies which do not grow in the presence of tetracycline.

pBR322 plasmid DNA (2 μg) was denatured by treatment with 0.2M NaOH and 0.2 mM EDTA for 5 minutes at 25° C. The pH was then neutralized by addition of 0.2M ammonium acetate pH 4.6. The DNA was then precipitated by addition of ethanol and isolated by centrifugation. The DNA pellet was dried and then resuspended in 100 μl of 10 mM Tris, pH 7.9, 1 mM EDTA. 10 μl (0.2 μg) of denatured template was used for each of two mutagenesis reactions.

In a first reaction, the denatured template was hybridized with oligonucleotide SEQ. ID. NO: 1 and a tetracycline knockout (tetKO) oligonucleotide, SEQ. ID. NO: 5 (see Table 1, below). In a second control reaction, the denatured template was hybridized to the tetKO oligonucleotide, SEQ. ID. NO: 5, alone. Hybridization reactions were performed in 20 μl reactions containing 20 mM Tris-HCl, pH 7.5, 10 mM MgCl₂, and 50 mM NaCl. Template and oligonucleotides were heated to 85° C. and cooled to 25° C. at approximately 1° C./minute. Reactions were then incubated with 10 units of T4 DNA polymerase and 3 units of T4 DNA ligase in the presence of 13 mM Tris-HCl, pH 7.5, 0.5 mM dNTPs, 1 mM ATP, 2 mM DTT, 6.7 mM MgCl₂, 33 mM NaCl in a total volume of 30 μl for 90 minutes at 37° C.

Aliquots of the two reactions were transformed into *E. coli.* cell line ES1301. This cell line contains a mutation in the mutS gene which reduces mismatch repair in the cell, which results in a higher percentage of the desired mutation. Transformations were performed by incubating 1.5 μl of the mutagenesis reactions with 100 μl of ES1301 cells made competent by the procedure described by Hanahan (1985), incorporated herein by reference in its entirety. Cells and DNA were incubated on ice for 10 minutes and then transferred to a 42° C. water bath for 50 seconds. The transformation mixes were then placed on ice for approximately 2 minutes and then added individually to 900 μl of LB and incubated for 1 hour at 37° C. 4 ml of LB (Luria broth, also known as Lenox broth) was then added and the 5 ml transformations were divided into 1 ml aliquots. Ceftazidime was added at 0, 0.5, 2, 10, or 20 μg/ml final concentration to the 1 ml aliquots.

After overnight incubation at 37° C., the cultures were examined for growth. The mutagenesis reaction containing the SEQ. ID. NO: 1 oligonucleotide showed growth at all concentrations of ceftazidime whereas the transformation from the control mutagenesis showed growth only at concentrations of ceftazidime of 2 μg/ml and below. This result demonstrates the ability of the SEQ. ID. NO: 1 oligonucleotide to confer increased resistance to ceftazidime.

Plasmid DNA was isolated from the mutagenesis reaction containing the SEQ. ID. NO: 1 oligonucleotide grown in the presence of 20 μg/ml of ceftazidime. This plasmid DNA was used to transform the *E. coli* cell line JM109. Transformants were plated on LB containing ampicillin, ceftazidime, or cefotaxime. Colonies were obtained in each case after incubation at 37° C. overnight. Individual colonies were then tested for resistance to ampicillin or tetracycline. All colonies were resistant to ampicillin demonstrating that the SEQ. ID. NO: 1 oligonucleotide mutation confers resistance to ceftazidime and cefotaxime without destroying resistance to ampicillin.

Of the colonies tested, 40 of 50 from the ampicillin plate were tetracycline sensitive, an 80% mutagenesis rate. 50 out of 50 colonies from the ceftazidime and cefotaxime plates were tetracycline sensitive demonstrating a 100% mutagenesis rate. The slightly lower rate observed when the transformants are plated on ampicillin is likely due to ES1301 cells harboring the wild-type pBR322 plasmid which is carried into the JM109 transformation. Plating the JM109 transformation on ceftazidime or cefotaxime prevents growth of the wild-type plasmid. The results from this experiment demonstrate a high efficiency of coupling of the selectable mutation in the β-lactamase gene with another mutant outside of that gene.

mutations and the wild-type β-lactamase allows for efficient selection of the G238S:E24OK:R241G mutations as well as secondary mutations outside the β-lactamase gene as demonstrated in Example 1.

Example 3

An essential part of the procedure is that the selective oligonucleotide (e.g., oligonucleotide SEQ. ID. NO: 1) must be on the same strand as the oligonucleotide used to create the desired mutation. The following example demonstrates this requirement.

The oligonucleotide SEQ. ID. NO: 2 encodes the same G238S:E24OK:R241G mutations to β-lactamase as the oligonucleotide SEQ. ID. NO: 1 except its sequence is the reverse complement of the SEQ. ID. NO: 1 oligonucleotide. Therefore, the SEQ. ID. NO: 2 oligonucleotide hybridizes to the opposite DNA strand than the SEQ. ID. NO: 1 oligonucleotide.

TABLE 1

Oligonucleotide Primers Used in the Examples.

| Oligonucleotide | Sequence | Function |
| --- | --- | --- |
| SEQ. ID. NO: 1 | CCGCGAGACCCACCCTTGGAGGCTCCAGATTTATC | G238S:E24OK:R241zG mutation in β-lactamase |
| SEQ. ID. NO: 2 | GATAAATCTGGAGCCTCCAAGGGTGGGTCTCGCGG | G238S:E24OK:R241G mutation in β-lactamase |
| SEQ. ID. NO: 3 | CGCCAGGGTTCCCAGTCACGACG | β-galactosidase α-peptide frameshift |
| SEQ. ID. NO: 4 | CGTCGTGACTGGGAACCCTGGCG | β-galactosidase α-peptide frameshift |
| SEQ. ID. NO: 5 | GCCGGGCCTCTTGCGGGCGTCCATTCC | tetracycline knockout (eteKO) sequence |

Example 2

The SEQ. ID. NO: 1 oligonucleotide encodes the G238S:E24OK:R241G mutations β-lactamase. These mutations confer resistance to ceftazidime and cefotaxime while retaining resistance to ampicillin. In order to determine the best concentrations of antibiotics to select for these mutations, a matrix of cefotaxime and ceftazidime concentrations was evaluated for selection of the G238S:E24OK:R241G triple mutant.

Figure 2:
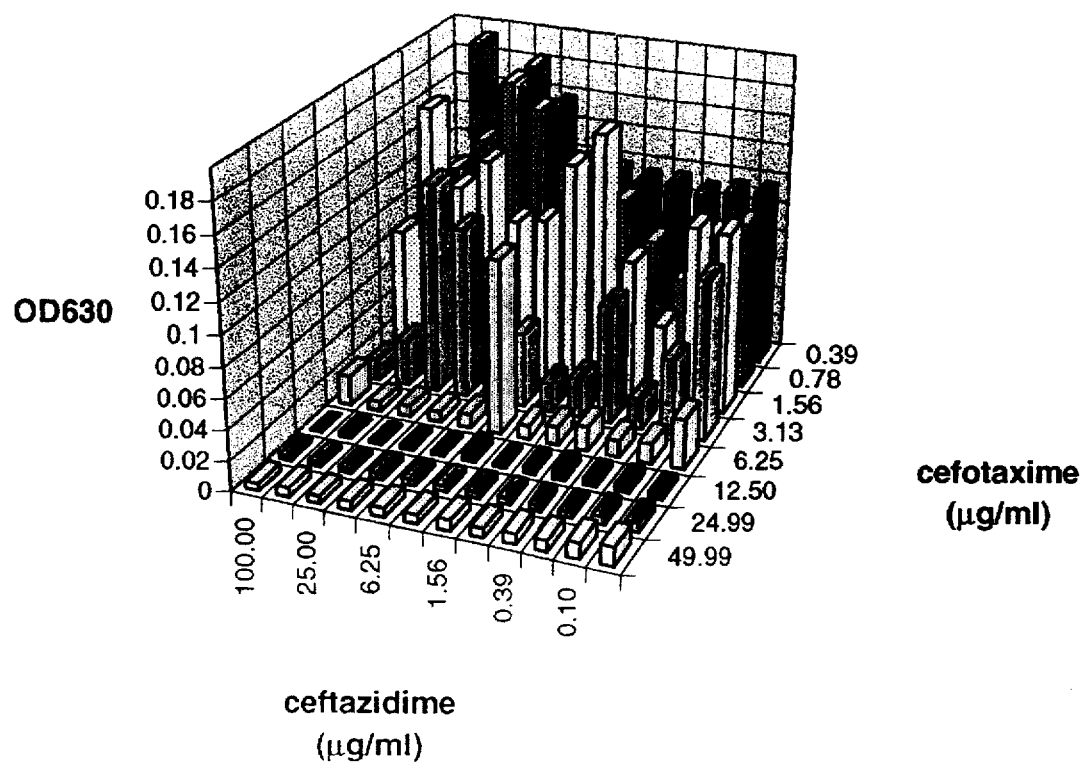
FIG. 2 is an antibiotic matrix depicting the effect of various concentrations of ceftazidime and cefotaxime on the growth of E. coli transformed with a plasmid containing a mutated β-lactamase gene using the present method as described in Example 2, below.

A matrix of antibiotic concentrations was established by performing serial dilutions of ceftazidime (0.05–100 µg/ml) and cefotaxime (0.39–50 µg/ml) in LB containing ampicillin (100 µg/ml) in a sterile microtiter dish. The matrix was then inoculated with a small amount of an ES1301 cell line transformed with either a control plasmid pKK223-3 derivative or the pKK223-3 derivative containing the G238S:E24OK:R241G mutations in β-lactamase. (See, for instance, Hanahan, supra.) Microtiter plates were incubated at 37° C. overnight and cell growth evaluated by measuring the optical density at 630 nm. The results are shown in FIG. 2. An identical control matrix was inoculated with wild-type E. coli. The results of the control reaction are shown in FIG. 1.

FIG. 2 clearly shows the increased resistance to ceftazidime and cefotaxime conferred by the G238S:E24OK:R241G mutations. This mutation can be selected in ceftazidime concentrations up to 100 µg/ml and cefotaxime concentrations up to 3.13 µg/ml. In contrast, the wild-type β-lactamase confers resistance to only up to 1.56 µg/ml ceftazidime and 0.39 µg/ml cefotaxime. (See FIG. 1.) This large differential between the G238S:E24OK:R241G Oligonucleotides SEQ. ID. NO: 3 and SEQ. ID. NO: 4 (see Table 1, above) encode frameshift mutations in the α-peptide of β-galactosidase commonly used for blue/white screening in DNA cloning vectors. Introduction of this frameshift mutation into the α-peptide causes inactivation of the α-peptide resulting in white versus blue colonies when introduced into an appropriate strain such as JM109 and plated on media containing isopropyl-1-thio-β-D-galactoside (IPTG) and 5-bromo-4-chloro-3-indolyl-β-D-galactoside (X-gal). This blue to white shift provides a convenient screen for mutagenesis efficiency. Oligonucleotides SEQ. ID. NO: 3 and SEQ. ID. NO: 4 hybridize to the same strand of the template as oligonucleotides SEQ. ID. NO: 1 and SEQ. ID. NO: 2, respectively, in the plasmid pGEM11Zf(+).

Mutagenesis reactions were performed as described in Example 1 using pGEM11Zf(+) (Promega Corporation, Madison, Wis.) as the plasmid template. The selective oligonucleotides (SEQ. ID. NO: 1 and SEQ. ID. NO: 2) were paired with the α-peptide mutagenic oligonucleotides (SEQ. ID. NO: 3 and SEQ. ID. NO: 4) to give the following combinations:

SEQ. ID. NO: 1/SEQ. ID. NO: 3
SEQ. ID. NO: 1/SEQ. ID. NO: 4
SEQ. ID. NO: 2/SEQ. ID. NO: 3
SEQ. ID. NO: 2/SEQ. ID. NO: 4.

Mutagenesis reactions were selected in a mixture of ampicillin (100 µg/ml), ceftazidime (25 µg/ml), and cefotaxime (1.5 µg/ml). Colonies were plated in the presence of IPTG and X-gal to allow blue/white screening. The results from the mutagenesis are shown in Table 2, below.

The results show a high efficiency (>70%) of mutagenesis in the α-peptide when the mutagenic oligonucleotide hybridizes to the same strand as the selective oligonucleotide (pairs SEQ. ID. NO: 1/SEQ. ID. NO: 3 and SEQ. ID. NO: 2/SEQ. ID. NO: 4) and no detectable mutagenesis (<1%) when selective and mutagenic oligonucleotides hybridize to opposite strands (pairs SEQ. ID. NO: 1/SEQ. ID. NO: 4 and SEQ. ID. NO: 2/SEQ. ID. NO: 3). The results show the dramatic improvement in mutagenesis efficiency when the alteration in substrate specificity of β-lactamase encoded by the selective oligonucleotides is paired with the desired mutagenic oligonucleotide.

TABLE 2

Mutagenesis Results from Example 3.

| Selective Oligonucleotide | Mutagenic Oligonucleotide | Hybridization to Same Strand | % Mutants |
|---|---|---|---|
| SEQ. ID. NO: 1 | SEQ. ID. NO: 3 | Yes | 73% |
| SEQ. ID. NO: 1 | SEQ. ID. NO: 4 | No | <1% |
| SEQ. ID. NO: 2 | SEQ. ID. NO: 3 | No | <1% |
| SEQ. ID. NO: 2 | SEQ. ID. NO: 4 | Yes | 75% |

It is understood that the present invention is not limited to the particular embodiments, reagents, steps, or methodologies described hereinabove, but embraces all such forms and modifications thereof as come within the scope of the attached claims.

BIBLIOGRAPHY

Bohnsack (1996), Methods in Molecular Biology: In vitro Mutagenesis Protocols; Vol. 57, M. K. Thrower, Ed., Humana Press Inc., Totowa, New Jersey.

*Current Protocols in Molecular Biology* (1994), Vol 1, Chapter 1.8, John Wiley and Sons, New York, New York.

Delaire, M., Labia, R., Samama, J. P., and Masson, J. M. (1992), The Journal of Biological Chemistry 267(29): 20600–20606.

Hanahan, D. (1985), In: DNA Cloning, Vol. 1, Glover, ed., IRL Press Ltd., London, 109.

Imtiaz et al. (1994), Antimicrobial Agents and Chemotherapy, (38)5: 1134–1139.

Lenfant et al. (1991), The Journal of Biological Chemistry, 266(26):17187–17194.

Palzkill and Botstein (1992a), PROTEINS: Structure, Function, and Genetics, 14:29–44.

Palzkill and Botstein (1992b), Journal of Bacteriology, 17:5237–5243.

Vandeyar et al. (1988), Gene, 65:129–133.

Venkatachalam et al. (1994), Characterization of TEM-1 β-lactamase Mutants From Positions 238 to 241 With Increased Catalytic Efficiency For Ceftazidime, *The Journal of Biological Chemistry,* 269(38):23444–23450.

---

What is claimed is:

1. A method for conducting site-specific mutagenesis of single or double-stranded nucleic acids comprising:
   (a) hybridizing a first mismatched oligonucleotide which encodes a mutation in an antibiotic resistance gene to a target nucleic acid strand;
   (b) hybridizing at least one other mismatched oligonucleotide encoding a desired mutation to the target nucleic acid strand; then
   (c) extending the hybridized mismatched oligonucleotides to yield an extended nucleic acid molecule; then
   (d) incorporating the extended nucleic acid molecule of step (c) into a host cell line to yield transformed cells; and then
   (e) separating the transformed cells from step (d) from non-transformed parent cells and cells lacking the mutation encoded by the first mismatched oligonucleotide via a differential antibiotic resistance conferred by the first mismatched oligonucleotide, whereby transformed cells containing the desired mutation are selected.

2. The method according to claim 1, wherein in step (a) the target nucleic acid strand is a deoxyribonucleic acid.

3. The method according to claim 1, wherein in step (a) the target nucleic acid strand is a ribonucleic acid.

4. The method according to claim 1, wherein in step (a) a first mismatched oligonucleotide encoding a mutation in β-lactamase is hybridized to the target nucleic acid.

5. The method according to claim 1, wherein in step (a) SEQ. ID. NO. 1 is hybridized to the target nucleic acid.

6. The method according to claim 1, wherein in step (a) SEQ. ID. NO. 2 is hybridized to the target nucleic acid.

7. The method according to claim 1, wherein in step (d) the extended nucleic acid molecule is incorporated into an *E. coli* cell.

8. The method according to claim 7, wherein in step (d) the extended nucleic acid molecule is incorporated into a mismatch repair-deficient *E. coli* cell.

9. The method according to claim 7, wherein step (d) the extended nucleic acid molecule is incorporated into an *E. coli* strain ES1301 cell.

10. The method according to claim 1, wherein in step (e), the transformed cells are separated via antibiotic resistance to cefotaxime.

11. The method according to claim 1, wherein in step (e), the transformed cells are separated via antibiotic resistance to ceftazidime.

12. An isolated deoxyribonucleic acid consisting of SEQ. ID. NO: 1.

13. An isolated mutant gene encoding a β-lactamase gene product which confers increased β-lactam antibiotic resistance to hosts transformed therewith comprising a nucleotide base sequence as shown in SEQ. ID. NO: 1.

14. A kit for conducting site-specific mutagenesis of single or double-stranded nucleic acids comprising a receptacle containing a DNA molecule selected from the group consisting of SEQ. ID NO: 1 and SEQ. ID. NO: 2.

* * * * *